United States Patent

Haas et al.

[11] Patent Number: 6,118,015
[45] Date of Patent: Sep. 12, 2000

[54] WATER-CONTAINING SOLUTIONS OF ACRYLIC-FUNCTIONALIZED ORGANOSILANES

[75] Inventors: Margaret Haas, Koenigswinter; Guenther Bernhardt, St. Augustin; Reinhard Matthes, Berg. Gladbach, all of Germany

[73] Assignee: Huels Aktiengesellschaft, Marl, Germany

[21] Appl. No.: 08/698,262

[22] Filed: Aug. 14, 1996

[30] Foreign Application Priority Data

Aug. 24, 1995 [DE] Germany .................. 195 31 144

[51] Int. Cl.[7] .................. C07F 7/08; C07F 7/18
[52] U.S. Cl. .............. 556/440; 106/287.13; 106/287.15; 106/287.16; 427/417; 427/595; 427/387; 427/407.2; 428/391; 428/425.5; 428/429
[58] Field of Search .............. 556/440; 106/287.13, 106/287.15, 287.16; 428/391, 425.5, 429; 427/487, 595, 387, 407.2

[56] References Cited

U.S. PATENT DOCUMENTS

| | | |
|---|---|---|
| 5,145,979 | 9/1992 | Takatsuna et al. .................. 556/440 |
| 5,543,538 | 8/1996 | Haas et al. . |
| 5,593,787 | 1/1997 | Dauth et al. .................. 428/447 |

FOREIGN PATENT DOCUMENTS

| | | |
|---|---|---|
| 0 340 816 | 11/1989 | European Pat. Off. . |
| 1 270 716 | 6/1968 | Germany . |
| 949126 | 2/1964 | United Kingdom . |

*Primary Examiner*—Paul F. Shaver
*Attorney, Agent, or Firm*—Oblon, Spivak, McClelland, Maier & Neustadt, P.C.

[57] ABSTRACT

The present invention relates to water-containing solutions of acrylic-functionalized organosilanes of the general formula I

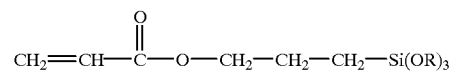

in which R is a methyl or ethyl group, having a starting-material concentration of organosilane of between 10 and 80% by weight. The present invention additionally relates to a process for the preparation of such water-containing solutions of acrylic-functionalized organosilanes and to their use, inter alia for coatings, surfaces or intermediate layers, which are obtainable by applying organosilane-containing compounds from a solution to a surface and by crosslinking by means of UV light.

21 Claims, No Drawings

WATER-CONTAINING SOLUTIONS OF ACRYLIC-FUNCTIONALIZED ORGANOSILANES

BACKGROUND OF THE INVENTION

1. Field of the Invention

The present invention relates to water-containing solutions of acrylic-functionalized organosilanes of the general formula I

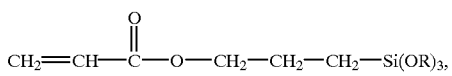

in which R is a methyl or ethyl group, to a process for their preparation and to their use, inter alia for coatings, surfaces or intermediate layers.

2. Description of the Background

DE-B 1 270 716 describes aqueous solutions of methacryloxy- and acryloxyalkyltrialkoxysilanes. The concentration of the organosilanols and -siloxanols in the aqueous solutions is given as being from around 0.1 to 10% by weight. Their use for the treatment of glass fibers or fiber structures produced therefrom, such as rovings, fabrics or mats, is mentioned in particular. A description is given both of dilute solutions of from 0.25 to 1.5% by weight organosilane, for producing finishes on size-free fabrics or rovings, and of from 5 to 10% strength by weight solutions, for sizing freshly spun glass fibers.

In this context, an immersion method is used to deposit, from dilute solutions, monomolecular or multilayer coats (finishes) on the glass fiber, which finishes are anchored firmly to the fiber surface by means of Si—OH groups, with the formation of siloxane bonds.

From 5 to 10% by weight solutions employed in concentrated form, which are used for example for treating glass fibers after the spinning operation, by drawing the fiber over rolls, moving belts or pads which are impregnated with the treatment solution, lead to the formation of a film (size) which may have a positive effect both on the processing properties, such as the lubricity of the fiber and its twisting to give folded yarn, cable yarn or sliver, and on the properties of the subsequent product.

Owing to the double bond of the acrylic or methacrylic function at the organic radical, the silane molecules anchored firmly to the fiber surface by way of the siloxane bond are able to copolymerize with other double bonds of unsaturated resin systems and, after curing of the resins, are firmly integrated into the coherent phase or resin matrix.

By means of the composite structure produced by the organosilane at the phase boundary between glass fibers, or structures produced from them, and the surrounding matrix, entirely new sets of properties can be achieved in the resins used; for example, enhanced mechanical strength, improved electrical properties and better protection against the penetration of moisture.

One deficiency, however, is that solutions based on 3-methacryloxypropyltrialkoxysilanes can be stored only for a limited time. Furthermore, DE-B 1 270 716 discloses only those aqueous solutions based on 3-methacryloxy- or acryloxyalkyltrialkoxysilane which have been prepared using up to around 10% by weight of organosilane. In Example 1 of DE-B 1 270 716, gentle shaking of 1 part of acryloxypropyltrimethoxysilane with 20 parts of 0.1% strength acetic acid produced a homogeneous hydrolysate which was subsequently diluted to a 0.5% strength solution by adding 179 parts of water.

The time for which such solutions can be stored is also referred to below as service life. For example, from 0.1 to 1% strength by weight aqueous solutions of 3-methacryloxypropyltrimethoxysilane become cloudy after only 2 days. As the concentration of organosilane rises, the service life is dramatically reduced, and for a 10% strength by weight aqueous solution is only around 15 hours. As the service life increases, the monomeric and/or oligomeric organosilanols initially present form cyclic and linear polycondensates. As the chain length grows further, the solubility concentration of the polycondensates is also exceeded. Thus the solution first becomes cloudy, and then flocculation takes place. Cloudy and flocculated solutions are unusable for the treatment of glass fibers or fabrics produced therefrom.

In industrial processes, especially continuous processes, for example, during the spinning of glass fibers, it is usually necessary after a short time to replace the unusable solutions with new solutions; this leads inevitably to the complex necessity of keeping stocks of the solutions, and constitutes a considerable cost factor. Added to this is the expense of disposing of the unusable solutions.

In the preparation especially of concentrated solutions of 3-methacryloxypropyltrialkoxysilanes, a disproportionately long dissolving time is necessary until the clear point of the solution is reached. Another disadvantage is that, at concentrations less than 10% by weight of 3-methacryloxypropyltrialkoxysilane, it is no longer possible to reach a clear point.

However, for certain glass fiber sizes which comprise film formers, antistats and wetting agents as well as the organosilane, higher concentrations of organosilane are of advantage.

The object of the invention was therefore to provide a clear, aqueous solution of an organofunctional silane, the intention being that the organosilane in water, or reaction products formed in this case, i.e. monomeric, oligomeric or even polymeric hydrolysates and condensates, should be present in as high a concentration as possible, the clear point time (CPT) being as short as possible and the solutions having maximum service lives (SL), i.e. remaining free from clouding over a relatively long period.

SUMMARY OF THE INVENTION

It has surprisingly been found that the use, instead of 3-methacryloxypropyltrialkoxysilanes, of 3-acryloxypropyltrialkoxysilanes for water-containing organosilane solutions with concentrations of starting material of between 10 and 80% by weight, based on the weight of the solution, not only leads to high solubilities of the orgoanosilane employed in water, with comparatively short clear point times, but also—and this is particularly surprising to the person skilled in the art—results in aqueous solutions of such organosilanes at such high concentrations being stable for a comparatively long time. The percentages disclosed relate in each case to the weight of the monomeric organosilane used as starting material for preparing the solution, based on the weight of the overall solution. These surprising results are obtained by preparing solutions of acrylic-functionalized organosilanes of the general formula I

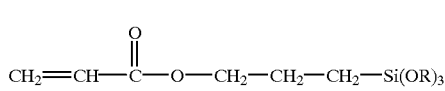

(I)

in which R is a methyl or ethyl group, by dissolving more than 10% by weight and less than 65% by weight of organosilane, based in each case on the weight of the solution, in acidified water, the process of dissolving comprising the initial introduction of acidified water or, in order to prepare highly concentrated solutions, of the organosilanes and addition of from 35 to 20% by weight of acidified water, based on the weight of the solution. Such solutions are generally prepared with thorough mixing and in the presence of air. The pH of the solutions is suitably in the range from 3 to 5, preferably in the pH range from 4 to 4.5. A carboxylic acid is preferably used to acidify the water. The clear point times of aqueous or aqueous/alcoholic solutions of acrylic-functionalized organosilanes of the general formula I which can be obtained in this way are, as a rule, reduced to one third, and the service lives are generally prolonged to from four to five times the value which is customary for commercial methacryloxyalkyalkoxysilane solutions.

DESCRIPTION OF THE PREFERRED EMBODIMENTS

The present invention therefore relates to water-containing solutions of acrylic-functionalized organosilanes of the general formula I

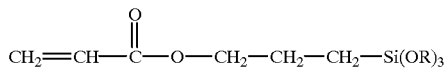

(I)

in which R is a methyl or ethyl group, having a starting-material concentration of organosilane of more than 10% by weight, in particular more than 15% by weight and, very particularly, more than 25% by weight, and less than 80% by weight.

The solutions according to the invention are preferably essentially alcohol-free or low in alcohol. The alcohol content is preferably from 0.01 to 10% by weight, particularly preferably from 0.1 to 2% by weight, based on the weight of the solution, alcohol in this context referring to methanol or ethanol or a mixture thereof.

The solutions according to the invention generally comprise at least one carboxylic acid whose $pK_a$ is preferably in the range from 3.7 to 5.0, examples being acetic acid, propionic acid, formic acid, acrylic acid and methacrylic acid.

The solutions according to the invention preferably have a pH of between 3 and 5 and, with particular preference, of between 3.5 and 4.5.

The present invention additionally relates to a process for the preparation of water-containing solutions of acrylic-functionalized organosilanes of the general formula I

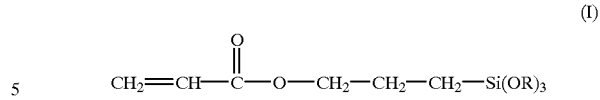

(I)

in which R is a methyl or ethyl group, which is characterized in that more than 10% by weight, preferably more than 15% by weight, particularly preferably more than 25% by weight and less than 65% by weight of organosilane, based in each case on the weight of the solution, is dissolved in acidified water or, for highly concentrated solutions, the organosilanes are initially introduced and from 35 to 20% by weight of acidified water is added, based on the weight of the solution. The term highly concentrated solutions in the context of the present invention is intended to refer to solutions prepared using between 65 and 80% by weight of organosilane, based on the weight of the solution.

In the process according to the invention it is preferable to employ acidified water with a pH of between 3 and 5, more preferably between 3.5 and 4.5, and even more preferably, between 4 and 4.5. The water is preferably acidified with a carboxylic acid whose $pK_a$ is in the range from 3.7 to 5.0, although other acids may also be employed, including for example inorganic acids such as hydrohalic acids, sulphuric acid or phosphoric acid.

In the process according to the invention the solution is suitably prepared with stirring, preferably in the presence of air.

In the process according to the invention, the dissolving times (clear point times) are in general between 40 minutes and 12 hours.

Should it be necessary, for certain applications, to prepare essentially alcohol-free or low-alcohol solutions, then in the process according to the invention, the alcohols, preferably methanol or ethanol, can be evaporated out of the solution according to the invention almost completely, or else only partially, under reduced pressure.

In general, the procedure adopted for the preparation of water-containing solutions in accordance with the process of the invention is that, when using more than 10% by weight and less than 65% by weight of acrylic-functionalized organosilanes of the general formula I, acidified water is initially introduced, the organosilane component is added, and thorough mixing is suitably carried out until a clear solution is obtained. The mixing operation is in general carried out at room temperature and in the presence of air. The organosilanes can be added to the initially introduced, acidified water in portions, for example dropwise or else in large portions or all at once. They are preferably added in large portions. Dissolution of the organosilanes in water generally takes place by hydrolysis, with the possibility of condensation reactions also taking place. The organosilanes are generally hydrolysed with agitation of the mixtures, preferably using a stirrer, in which case the stirrer mechanism is generally started up before adding the organosilane.

In the process according to the invention, for highly concentrated solutions—i,e., solutions prepared using from 65 to 80% by weight of organosilanes of the general formula I—the organosilanes are initially introduced and from 35 to 20% by weight of acidified water is added, based on the weight of the overall solution. Thorough mixing is suitably carried out until a clear solution is obtained. Here too, it is possible to operate at room temperature and in the presence of air. The addition of acidified water to the initial organosilane charge in this case is also made preferably in portions and suitably with stirring.

For the purpose of stabilization against premature polymerization, oxygen or an oxygen-containing gas can be bubbled through. If desired it is possible to introduce additional inhibitors, preferably water-soluble inhibitors, provided they do not have an adverse effect on the subsequent use of the solutions. Examples of suitable stabilizers are hydroquinone or hydroquinone monomethyl ether.

In general, the hydrolysis or condensation of the organosilanes of the general formula I leads to formation of monomeric, oligomeric and/or polymeric reaction products release of alcohol R—OH; for example:

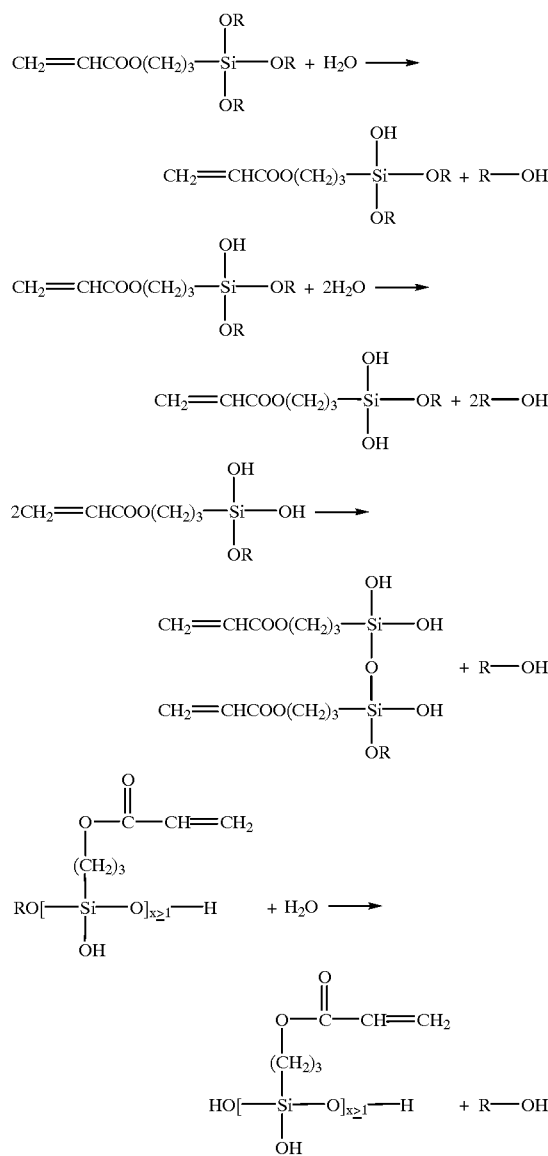

As the concentration of organosilane employed rises, these reactions are generally accompanied by the production not only of the water not consumed in hydrolysis but also of increasing quantities of alcohol as cosolvent. Water and alcohol can make up equal proportions of the solvent or else, respectively, the predominant proportion of the solvent. Thus, in the case of solutions with low concentrations of organosilane, it is generally the water component which predominates in the solvent, while in the case of high concentrations of organosilane it is the alcohol component which is predominant.

In the process according to the invention, however, it is also possible to prepare relatively highly concentrated solutions with a low proportion of alcohol by evaporating the alcohol component, suitably under reduced pressure and preferably at as low a temperature as possible. In order to keep the content of monomeric, oligomeric and/or polymeric organosilane-containing compounds in the solution substantially constant, when removing the alcohol from the solution it is possible to compensate for the loss of solvent by adding appropriate quantities of water, suitably acidified water, in other words preferably maintaining the prevailing pH of the solution. The residual alcohol content may be between 0.01 and 10% by weight based on the overall solution, preferably between 0.1 and 2% by weight. The removal of the alcohol from the solution can be undertaken in any appropriate vacuum-proof apparatus. The operating pressure can be between 1 and 400 mbar absolute, and is preferably between 5 and 100 mbar absolute. In accordance with the chosen pressure the operating temperature can be from 5 to 40° C., preferably 10 to 30° C.

The present invention also relates to the use of a water-containing solution of an acrylic-functionalized organosilane of the general formula I, having a starting-material concentration of organosilane of between 10 and 80% by weight, or of a water-containing solution of an acrylic-functionalized organosilane of the general formula I, prepared by either (1) dissolving between 10 and 65% by weight of organosilane, based on the weight of the solution, in acidified water or, (2) adding from 35 to 20% by weight of acidified water to between 65 and 80% by weight of organosilane, based on the weight of the solution, for the finishing of glass fibers and for the preparation of glass fibers with a size.

The organosilane-containing compounds can be applied from a solution according to the invention to glass fibers or structures produced therefrom; these fibers or structures can subsequently be bonded firmly, for example using unsaturated resins, in which case the resin composition expediently comprises at least one unsaturated polyester and/or acrylic resin. Should it be required by the particular application, the solutions according to the invention can be diluted by adding an appropriate solvent; examples of suitable solvents are water, acidified water, methanol, ethanol or another water-miscible alcohol.

However, the organosilane-containing compounds of the solutions according to the invention can also be applied, for example, to metallic and/or silicate surfaces. Silicate or metallic surfaces treated in this way generally have, in combination with unsaturated resins cured by peroxide, equal or even improved adhesive strength in comparison with surfaces treated with corresponding solutions of 3-methacryloxypropyltrialkoxysilanes.

It has additionally been found that coatings deposited on silicate and/or metallic surfaces from the novel aqueous or aqueous/alcoholic solutions of organosilanes of the general formula I can be crosslinked by means of UV light to form virtually insoluble structures.

Consequently, the present invention additionally relates to the use of a water-containing solution of an acrylic-functionalized organosilane of the general formula I, having a starting-material concentration of organosilane of between 10 and 80% by weight, or of a water-containing solution of an acrylic-functionalized organosilane of the general formula I, prepared by either (1) dissolving between 10 and 65% by weight of organosilane, based on the weight of the solution, in acidified water or, (2) adding from 35 to 20% by weight of acidified water to between 65 and 80% by weight of organosilane, based on the weight of the solution, characterized in that the organosilane-containing compounds of a solution, applied to a surface, are crosslinked by means of UV light. By crosslinking using UV light it is possible in this way to obtain coatings or surfaces or intermediate layers, for example as adhesion promoters; hard and substantially insoluble coatings can suitably be obtained in this way.

The novel water-containing solutions are generally clear solutions with good storage properties and can be prepared in a simple manner.

Having generally described this invention, a further understanding can be obtained by reference to certain specific examples which are provided herein for purposes of illustration only and are not intended to be limiting unless otherwise specified.

EXAMPLES

Examples 1 to 4

250 g portions of acidified water (pH 4.5) containing acetic acid were initially introduced, 3-acryloxypropyltrimethoxysilane (ACMO) (44.1 g; 62.5 g; 83.3 g and 217.9 g; respectively) was added all at once with stirring at room temperature and in the presence of air, dissolution was carried out until the solution was completely clear, and the CPT and SL of the solutions were determined. The pH of solutions prepared in this way was in the range from 4.3 to 4.5. The results are listed in Table 1, with the percentages by weight relating to the overall solution.

Comparison Examples A to D

In each case, different quantities of 3-methacryloxypropyltrimethoxysilane (MEMO) starting material were dissolved as far as possible in 250 g portions of acidified water (pH 4.5) containing acetic acid, with stirring at room temperature and in the presence of air, and the CPT and SL were determined in each case. The results are likewise given in Table 1, with the percentages by weight relating here, too, to the overall solution.

TABLE 1

| Examples | ACMO [% by weight] | CPT [min] | SL [d] |
| --- | --- | --- | --- |
| 1 | 15 | 48 | 4.5 |
| 2 | 20 | 60 | 4.5 |
| 3 | 25 | 65 | 6.5 |
| 4 | 35 | 73 | 14.5 |

| Comparison Examples | MEMO [% by weight] | CPT [min] | SL [d] |
| --- | --- | --- | --- |
| A | 5 | 80 | 3.5 |
| B | 7 | 105 | 3 |
| C | 10 | 133 | 2 |
| D | 20 | insoluble; highly cloudy solution | |

Example 5

20% strength by weight solutions of 3-acryloxypropyltrimethoxysilane (ACMO) were prepared in water at different pH levels, using acetic acid, and the clear point time (CPT) and service life (SL) were determined as a function of the pH. The results are listed in Table 2.

TABLE 2

| pH of the hydrolysis medium | CPT [min] | SL [d] |
| --- | --- | --- |
| 2.5 | 13 | 0.2 |
| 3.0 | 15 | 0.8 |
| 3.5 | 18 | 2.8 |
| 4.0 | 36 | 4.5 |
| 4.5 | 60 | 4.2 |
| 5.0 | 64 | 3.7 |

Example 6

21 g of 3-acryloxypropyltriethoxysilane (ACEO) were added with stirring to 179 g of water with a pH of 3.5 (containing acetic acid) at room temperature and in the presence of air in a 250 ml glass beaker. After 2 hours, a clear solution had formed which remained free from clouding for around 3½ days.

Comparison Example E 21 g of 3-methacryloxypropyltriethoxysilane (MEEO) were added with stirring to 179 g of water with a pH of 3.5 (containing acetic acid) at room temperature and in the presence of air in a 250 ml glass beaker. After stirring for 2 days, the mixture was still heavily clouded.

Example 7

125 g of 3-acryloxypropyltrimethoxysilane (ACMO) were added rapidly with stirring to 125 ml of water with a pH of 4.0 (containing acetic acid) at room temperature and in the presence of air in a 250 ml glass beaker. After 1.4 hours, a clear solution had formed. This solution was transferred to a round-bottomed flask fitted with thermometer, glass capillary tube, Claisen bridge and a receiver which was cooled with dry ice, and the methanol was evaporated by reducing the pressure (15 mbar) and bubbling in air, at an internal flask temperature of 25° C. After 2 hours, GC analysis of the solution remaining in the flask showed a methanol content of <0.3%. The aqueous solution of the organosilane remained free from clouding for more than 24 hours.

Example 8

160 g of 3-acryloxypropyltrimethoxysilane (ACMO) were initially introduced into a 250 ml glass beaker at room temperature and in the presence of air, 40 g of water with a pH of 4.0 (containing acetic acid) were added rapidly, and mixing was carried out using a stirrer. After 10 hours, a clear solution had formed. The solution remained free from clouding for more than 180 days.

Comparison Example F

A mixture of 160 g of 3-methacryloxypropyltriethoxysilane (MEMO) and 40 g of water with a pH of 4.0 (containing acetic acid) was stirred in a 250 ml glass beaker. After 2 days of stirring, no clear, homogeneous solution had been formed. When the stirrer was switched off, the phases separated again immediately.

Example 9

50 ml of the solution prepared in Example 8 were diluted with 10 ml of methanol (chemically pure) and, after adding 35 mg of benzoin, a microscope slide free from grease and dust was dipped into the diluted solution and, after a brief dripping period (angle of inclination 45°), was dried for one day in air and then for one hour under nitrogen in a vacuum of 1 mbar at up to 50° C. The glass plate treated in this way was irradiated for 0.5 hour in an exposure box using a mercury lamp (model Q 400 from Original Hanau Quarzlampen) under a nitrogen atmosphere (distance between lamp and slide: 30 cm). By this method it was possible, for example, to coat the surface of the slide with a tack-free and substantially scratch-proof coating.

Comparison Example G

A microscope slide free from grease and dust was treated with an undiluted aqueous solution of 3-methacryloxysilane in accordance with Comparison Example C which contained an additional 0.05% by weight of benzoin, based on the silane employed, and, after a short period of dripping and drying in air for one day, was after treated for one hour under nitrogen in a vacuum of 1 mbar at up to 50° C. It was then irradiated in a lightbox for 0.5 hour using a Q 400 mercury lamp under a nitrogen atmosphere, the distance between slide and light source being 30 cm. After this, the coating on the surface of the slide was still soft and tacky.

Example 10

A microscope slide free from grease and dust was treated with a 3-day-old aqueous solution of 3-acryloxypropyltrimethoxysilane (ACMO) from Example 1 and, after drying in air for one day and then in a vacuum cabinet for one hour, the slide was coated, using a doctor blade, with a 1 mm layer of styrene-containing UP resin (PALATAL® A 410, commercial product from BASF) which contained 2 g of cobalt octoate and 1 g of acetylacetone peroxide per 100 g of resin. After storage under a $CO_2$ atmosphere for one hour, the coated slide was subjected to thermal aftertreatment at 100° C. for 2 hours. After the one-hour boiling test, there was no separation of the resin coat from the glass.

Comparison Example H

A microscope slide free from grease and dust was treated with a 3-day-old, clouded, aqueous solution of 3-methacryloxypropyltrimethoxysilane from Comparison Example C and, after drying in air for one day and then in a vacuum cabinet for one hour, the slide was coated, using a doctor blade, with a 1 mm layer of styrene-containing UP resin (PALATAL® A 410, commercial product from BASF) which contained 2 g of cobalt octoate and 1 g of acetylacetone peroxide per 100 g of resin. After storage under a $CO_2$ atmosphere for one hour, the coated slide was subjected to thermal aftertreatment at 100° C. for 2 hours. When the specimen was treated in boiling water, the resin coat became detached from the glass after only a few minutes.

Definitions

The clear point time (CPT) is measured from the commencement of the mixing of water and silane until the solution is free from clouding.

The service life (SL) of the solution is measured from the beginning of the clear point until the solution becomes clouded. The solution is considered to be cloudy when the page of a book held behind the vessel, with a vessel diameter of from 8 to 10 cm, can no longer be read.

The disclosure of German priority patent application 195 31 144.2, filed Aug. 24, 1995, is hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A water-containing solution of an acrylic-functionalized organosilane of the general formula I

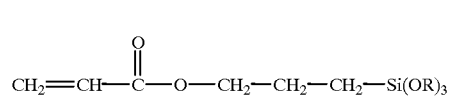

in which R is a methyl or ethyl group, having a starting-material concentration of organosilane of between 15 and 80% by weight.

2. The water-containing solution of an acrylic-functionalized organosilane according to claim 1, wherein the solution contains 10% by weight or less of alcohol.

3. The water-containing solution of an acrylic-functionalized organosilane according to claim 1, wherein the solution contains at least one carboxylic acid.

4. The water-containing solution of an acrylic-functionalized organosilane according to claim 1, wherein the pH is between 3 and 5.

5. A process for the preparation of a water-containing solution of an acrylic-functionalized organosilane according to claim 1, comprising either (1) dissolving between 15 and 65% by weight of organosilane, based on the weight of the solution, in acidified water or, (2) adding from 35 to 20% by weight of acidified water to between 65 and 80% by weight of organosilane, based on the weight of the solution.

6. The process according to claim 5, wherein the acidified water has a pH of between 3 and 5.

7. The process according to claim 5, wherein the water is acidified with a carboxylic acid whose $pK_a$ is in the range from 3.7 to 5.0.

8. The process according to claim 5, wherein the solution is prepared with stirring.

9. The process according to claim 5, wherein the solution is prepared in the presence of air.

10. The process according to claim 5, wherein the dissolving time is between 40 minutes and 12 hours.

11. The process according to claim 5, which additionally comprises evaporating essentially completely or partially, under reduced pressure, alcohols which have formed, out of the solution.

12. A process for finishing glass fibers or preparing glass fibers with a size comprising applying to said fibers the solution of claim 1.

13. A process for finishing glass fibers or preparing glass fibers with a size comprising applying to said fibers the solution prepared by the process of claim 5.

14. A process of coating a surface comprising applying the solution of an acrylic-functionalized organosilane of the general formula I of claim 1 to said surface, and then cross-linking said organosilane with UV light.

15. A process of coating a surface comprising applying the solution of an acrylic-functionalized organosilane of the general formula I prepared by the process of claim 5 to said surface, and then crosslinking said organosilane with UV light.

16. Glass fibers prepared by the process of claim 12.

17. Glass fibers prepared by the process of claim 13.

18. An article comprising a coated surface prepared by the process of claim 14.

19. An article comprising a coated surface prepared by the process of claim 15.

20. The article of claim 18 additionally containing another coating over said coated surface.

21. The water-containing solution of an acrylic-functionalized organosilane according to claim 1, wherein the starting-material concentration of organosilane is more than 25% by weight.

* * * * *

UNITED STATES PATENT AND TRADEMARK OFFICE
CERTIFICATE OF CORRECTION

PATENT NO. : 6,118,015
DATED : September 12, 2000
INVENTOR(S) : Margret Haas, et al.

It is certified that error appears in the above-identified patent and that said Letters Patent is hereby corrected as shown below:

On the title page, Item [75], the 1st Inventor's name is spelled incorrectly. Item [75] should read as follows:

---[75] Inventors: Margret Haas, Koenigswinter;
Guenther Bernhardt, St. Augustin;
Reinhard Matthes, Berg. Gladbach, all of Germany ---

Signed and Sealed this

Fifteenth Day of May, 2001

Attest:

NICHOLAS P. GODICI

*Attesting Officer*    *Acting Director of the United States Patent and Trademark Office*